(12) United States Patent
Angott

(10) Patent No.: US 8,475,377 B2
(45) Date of Patent: Jul. 2, 2013

(54) MULTI-MODALITY BREAST CANCER TEST SYSTEM

(75) Inventor: Paul G. Angott, Bloomfield Hills, MI (US)

(73) Assignee: First Sense Medical, LLC, Pontiac, MI (US)

(*) Notice: Subject to any disclaimer, the term of this patent is extended or adjusted under 35 U.S.C. 154(b) by 301 days.

(21) Appl. No.: 12/892,674

(22) Filed: Sep. 28, 2010

(65) Prior Publication Data

US 2011/0077523 A1 Mar. 31, 2011

Related U.S. Application Data

(60) Provisional application No. 61/246,202, filed on Sep. 28, 2009.

(51) Int. Cl.
  *A61B 8/00* (2006.01)
(52) U.S. Cl.
  USPC .......................................... 600/437; 600/473
(58) Field of Classification Search
  USPC .................................. 600/407, 437, 473, 476
  See application file for complete search history.

(56) References Cited

U.S. PATENT DOCUMENTS

| | | | |
|---|---|---|---|
| 4,170,987 A | 10/1979 | Anselmo et al. | |
| 4,341,222 A * | 7/1982 | Gardineer et al. | 600/437 |
| 4,428,382 A | 1/1984 | Walsall et al. | |
| 4,541,279 A | 9/1985 | Schomberg | |
| 4,570,638 A | 2/1986 | Stoddart et al. | |
| 5,083,073 A | 1/1992 | Kato | |
| 5,139,025 A | 8/1992 | Lewis et al. | |
| 5,590,653 A * | 1/1997 | Aida et al. | 600/411 |
| 5,709,206 A * | 1/1998 | Teboul | 600/437 |
| 5,782,767 A | 7/1998 | Pretlow, III | |
| 5,908,383 A * | 6/1999 | Brynjestad | 600/300 |
| 5,984,870 A | 11/1999 | Giger et al. | |
| 6,086,247 A | 7/2000 | von Hollen | |
| 6,117,080 A | 9/2000 | Schwartz | |
| 6,733,448 B2 | 5/2004 | Kelly et al. | |
| 6,825,838 B2 | 11/2004 | Smith et al. | |
| 7,154,397 B2 | 12/2006 | Zerhusen et al. | |
| 2004/0097811 A1 | 5/2004 | Smith et al. | |
| 2004/0138559 A1* | 7/2004 | Cheng et al. | 600/437 |
| 2007/0058845 A1 | 3/2007 | Diakides et al. | |
| 2008/0077005 A1* | 3/2008 | Piron et al. | 600/411 |
| 2008/0287750 A1* | 11/2008 | Hashimshony et al. | 600/301 |
| 2009/0240150 A1 | 9/2009 | Wang et al. | |

* cited by examiner

*Primary Examiner* — Jonathan Cwern
(74) *Attorney, Agent, or Firm* — Dickinson Wright PLLC

(57) ABSTRACT

A multi-modality breast cancer test assembly (20) of the type for detecting the position of potential breast cancer by performing thermography and optical spectroscopy and ultrasound tests (64). A contour recorder (108) takes and stores a contour-shape of the breast and a first contour analysis program (110) analyzes the contour-shape to generate and store a 3D model (112) of the breast having at least one testing coordinate (114) relative to a mass of the breast. At least one diagnostic program (122, 124, 126) initiates the diagnostic tests (60, 62, 64) at the at least one testing coordinate (114) and a data analysis program (128) analyzes the spatial interrelationship of the tests (60, 62, 64) at the testing coordinate (114) to detect the spatial position of a potential breast cancer within the breast.

9 Claims, 5 Drawing Sheets

MULTI-MODALITY BREAST CANCER TEST SYSTEM

CROSS REFERENCE TO RELATED APPLICATION

This application claims the benefit of provisional application Ser. No. 61/246,202 filed Sep. 28, 2009, entitled a "Multi-Modality Breast Cancer Test."

BACKGROUND OF THE INVENTION

1. Field of the Invention

A multi-modality breast cancer test of the type for detecting the position of potential cancer in a breast of a patient being supported in a prone position along an examination table in an examination room.

2. Description of the Prior Art

The multi-modality breast cancer test assemblies to which the subject invention pertains are assemblies which include a test unit having an interior for receiving the breast of the patient. Once such assembly is illustrated in U.S. Patent Application 2008/0077005 to Piron wherein a diagnostic assembly is disposed within the interior of the test unit and in electrical communication with a computer and includes a plurality of sensors for performing a plurality of diagnostic tests each having a different modality on the breast. It is well known for the computer to include a processor and a memory and a plurality of computer programs.

Additionally, it is common to have a contour recorder for taking and storing a contour-shape of the breast, as illustrated in U.S. Pat. No. 6,825,838 to Smith, wherein a first contour analysis program analyzes the contour-shape to generate and store a 3D model of the breast having at least one testing coordinate relative to a mass of the breast. The plurality of computer programs includes at least one diagnostic program for initiating the diagnostic test at the at least one testing coordinate.

Although the prior art multi-modality breast cancer test assemblies are able to perform a plurality of diagnostic tests each having a different modality on the breast, there remains a need for a cross-analysis of the modalities which reduces time, labor, and cost while correspondingly improving accuracy of the analysis.

SUMMARY OF THE INVENTION

The invention provides for a data analysis program for analyzing the spatial interrelationship of the plurality of diagnostic tests at the testing coordinate to detect the spatial position of a potential breast cancer within the breast.

The invention also provides for a method of analyzing the spatial relationship of the plurality of diagnostic tests at the testing coordinate to detect the spatial position of a potential breast cancer within the breast.

ADVANTAGES OF THE INVENTION

The analysis of the diagnostic tests using a data analysis program eliminates human error and improves the sensitivity of detecting the position of potential cancer in the breast. In addition, the cross-analysis of diagnostic data from the diagnostic tests each having a different modality at each of the precise testing coordinates can reduce false negatives because when one modality may miss the detection of potential breast cancer, another modality is able to detect it. Correspondingly, by performing a plurality of modalities, the diagnostic analysis program is able to increase the positive detection of breast cancer. In addition, since the robotic arm is placed with pin-point accuracy at each of the testing coordinates, the data analysis program is able to precisely interrelate the plurality of diagnostic tests at the testing coordinate. In other words, each of the different tests are performed relative to the same testing coordinate for improving the cross-analysis of the diagnostic data. Accordingly, the data analysis program optimizes the test results for detecting the position of potential cancer in a breast.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
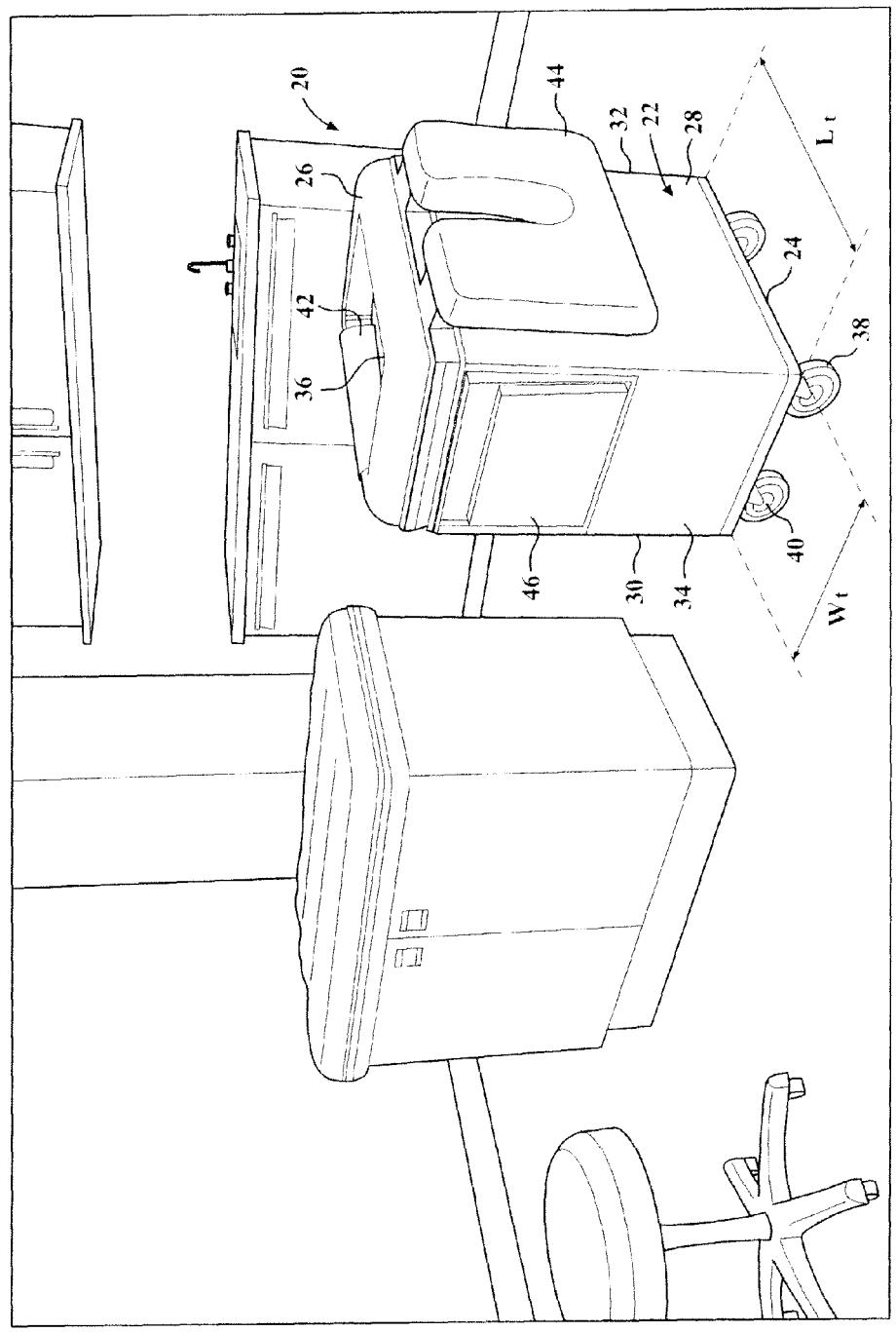
FIG. 1 is a perspective view of a multi-modality breast cancer test assembly showing a test unit and an examination table.
Figure 2:
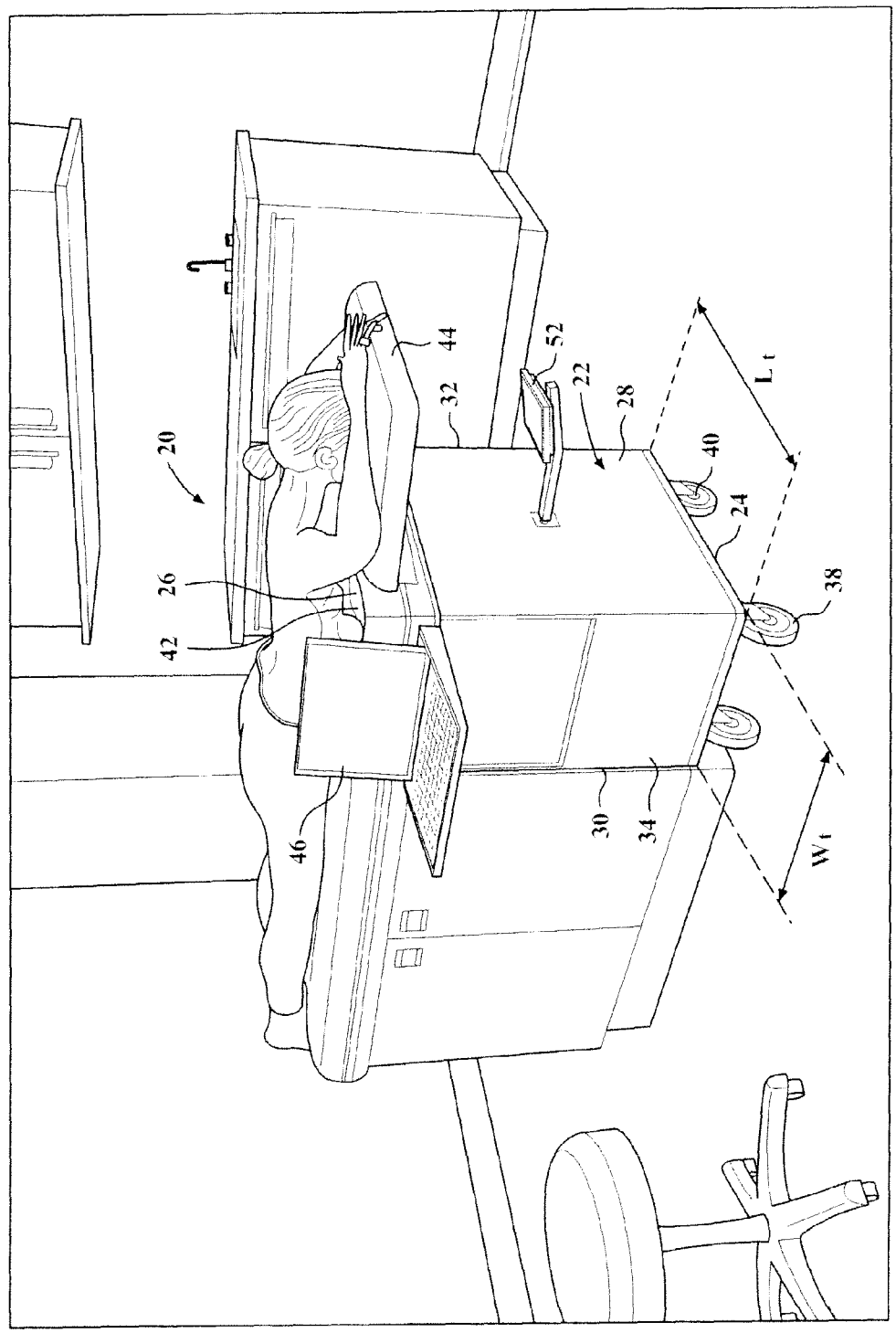
FIG. 2 is a perspective view of the multi-modality breast cancer test assembly showing the test unit in abutting relationship with the examination table for receiving a patient in a prone position along the examination table and a top surface of the test unit and showing a computer connected to the test unit.
Figure 3:
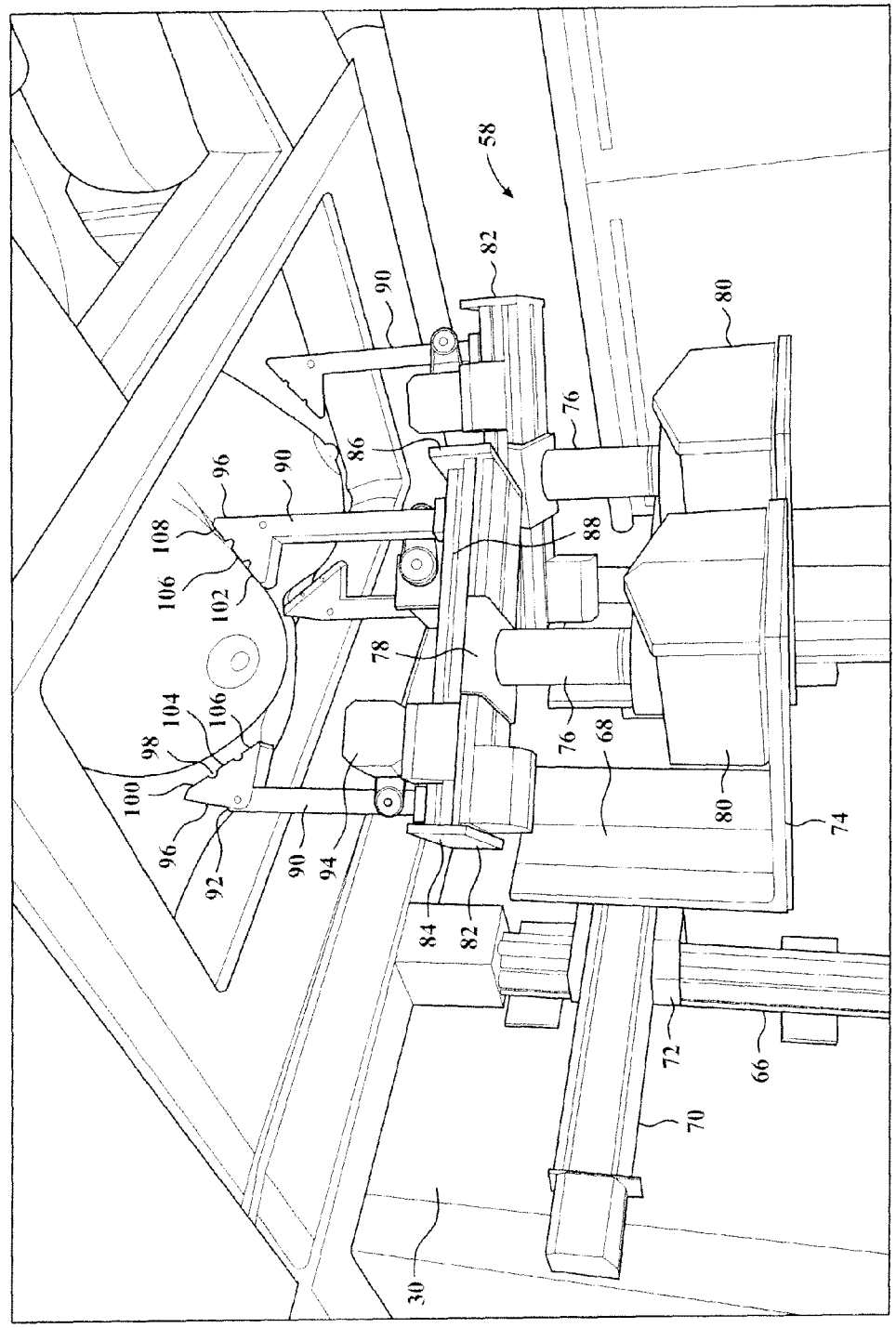
FIG. 3 is a perspective view of an interior of the test unit showing a diagnostic assembly including at least one robotic arm for receiving a plurality of sensors to perform a plurality of diagnostic tests each having a different modality on a breast.
Figure 4:
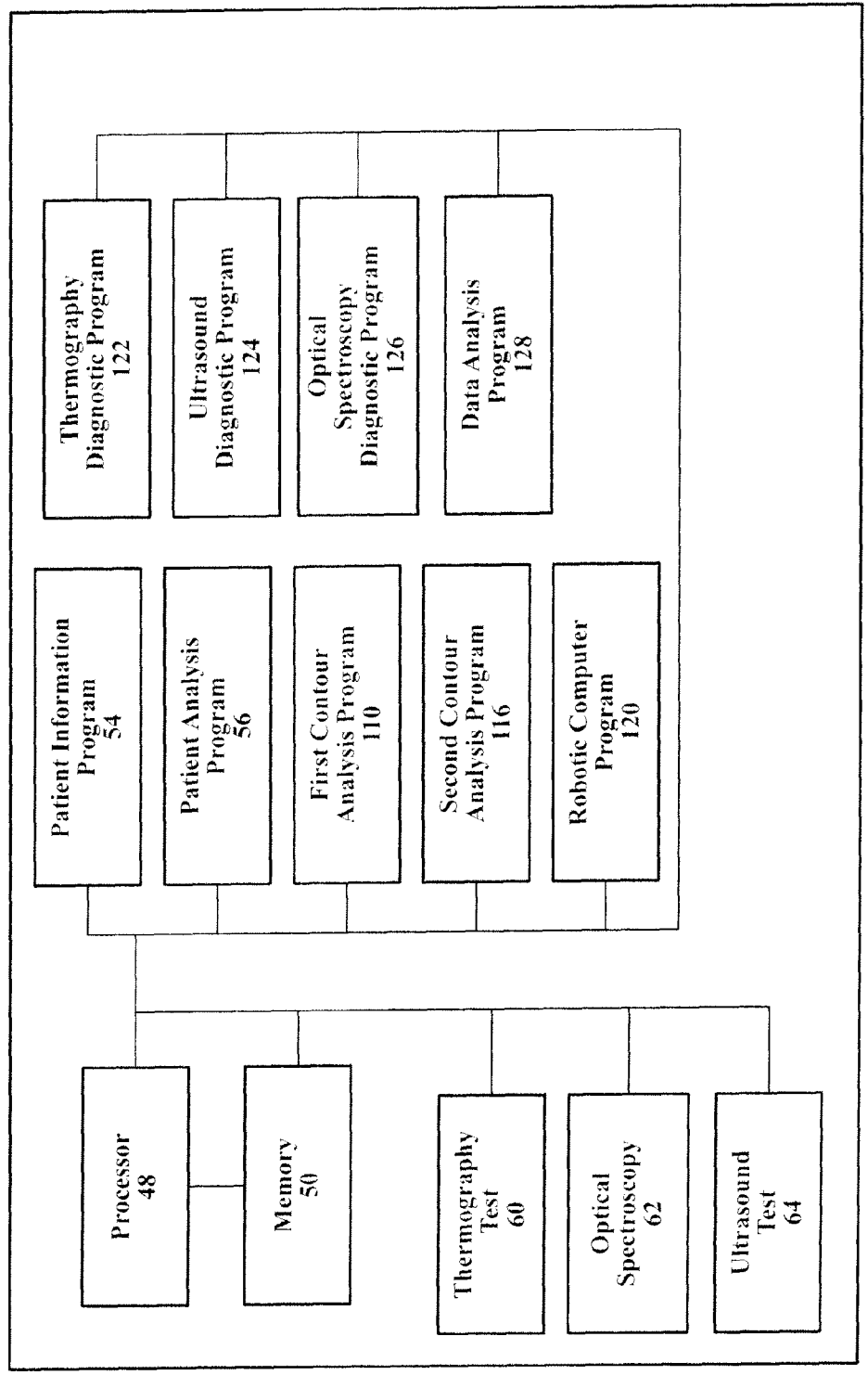
FIG. 4 is a schematic diagram of the computer showing a processor and a memory and a plurality of computer programs.
Figure 5:
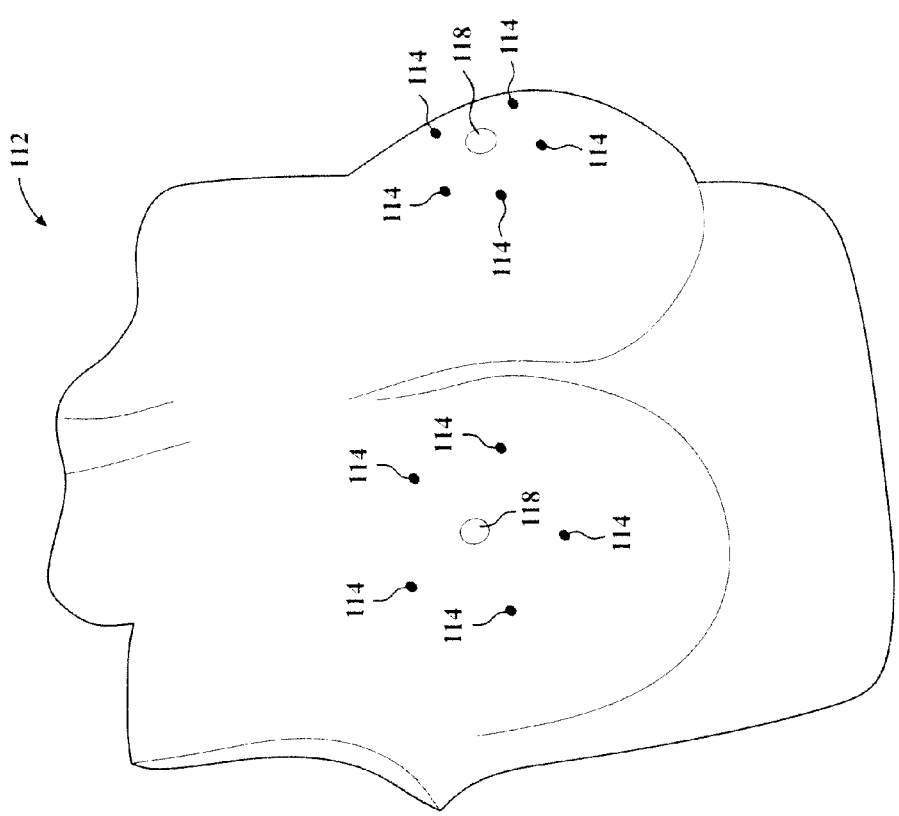
FIG. 5 is a perspective view of a 3D model of the breast showing at least one testing coordinate and a primary reference point of the breast.

Referring to the Figures, wherein like numerals indicate corresponding parts throughout the several views, a multi-modality breast cancer test assembly 20 of type for detecting the position of potential cancer in a breast of a patient being supported in a prone position along an examination table in an examination room is generally shown in FIGS. 1 and 2.

The assembly 20 includes a test unit 22 being rectangular and extending between a bottom surface 24 and a top surface 26 to define front and rear sides 28, 30 having a test unit length $L_t$ being less than or equal to 36 inches and left and right sides 32, 34 having a test unit width $W_t$ being less than or equal to 25 inches. The test unit 22 also includes an interior 36 being hollow and disposed inwardly from the surfaces 24, 26 and the sides 28, 30, 32, 34. A plurality of caster wheels 38 are attached to the bottom surface 24 for establishing rolling movement over ground in the examination room to dispose the rear side 30 of the test unit 22 in abutting relationship with the examination table for receiving the patient in the prone position along the top surface 26 of the test unit 22. Each of the caster wheels 38 include a locking mechanism 40 for preventing movement of the test unit 22 after it is disposed in abutting relationship with the examination table. The top surface 26 of the test unit 22 defines a window opening 42 for pendantly receiving the breast of the patient within the interior 36 of the test unit 22 when the patient is in the prone position. The size and shape of the test unit 22 is advantageous because it is movable between multiple examination rooms and also reduces the space requirements and cost of the test unit 22.

The test unit 22 includes a face support 44 hingedly attached to the front side 28 of the test unit 22 and is disposed next adjacent the top surface 26 for supporting a head of the patient in the prone position. A computer 46 is connected to the test unit 22 and includes a processor 48 and a memory 50 and a plurality of computer programs 54, 56, 110, 116, 120, 122, 124, 126, 128. A graphical user interface 52 extends outwardly from the front side 28 of the test unit 22 and is disposed below the face support 44 and in electrical communication with the computer 46 for establishing communication with the patient disposed in the prone position. The plurality of computer programs include a patient information program 54 for displaying a questionnaire on the computer 46, or alternatively on a designated website or a tablet pc, and receiving a plurality of patient inputs in response to the questionnaire for storage within the memory 50 of the computer 46. Examples of the patient inputs include family historical data of the patient that impacts breast cancer probability along with personal data which includes medicines, weight, and other factors affecting breast cancer risk. The plurality of computer programs 54, 56, 110, 116, 120, 122, 124, 126, 128 also include a patient analysis program 56 for evaluating the patient inputs and generating a start signal in response to completing the evaluation. In addition, during operation, the graphical user interface 52 is able to describe the details of the test to the patient and explain the benefits of early detection of breast cancer.

A diagnostic assembly 58 is disposed within the interior 36 of the test unit 22 and is in electrical communication with the computer 46 for performing a plurality of diagnostic tests 60, 62, 64 on the pendant breast in response to the start signal. In the preferred embodiment, the plurality of diagnostic tests 60, 62, 64 include a thermography test 60 and an optical spectroscopy test 62 and an ultrasound test 64.

The diagnostic assembly 58 includes at least one mechanical support 66 extending along the rear side 30 of the test unit 22 between the top surface 26 and the bottom surface 24 for supporting the diagnostic assembly 58 within the interior 36 of the test unit 22. The diagnostic assembly 58 also includes a base member 68 disposed about the mechanical support 66. The base member 68 includes a cross member 70 disposed in sliding engagement with the mechanical support 66 and extending perpendicularly to the mechanical support 66. The cross member 70 has a first motor assembly 72 in communication with the computer 46 and mechanically coupled with the mechanical support 66 for moving the base member 68 along the support from an initial resting position wherein the diagnostic assembly 58 is disposed next adjacent the bottom surface 24. The base member 68 also includes a base plate 74 disposed about the cross member 70.

A plurality of support posts 76 extend upwardly from the base plate 74 to a rail end 78 and each of the support posts 76 include a second motor assembly 80 in communication with the computer 46 for establishing at least 270 degree rotational movement of the support posts 76. Each of the support posts 76 include a support rail 82 extending perpendicularly about the rail end 78 between a first end 84 and a second end 86 and have tracks 88 extending therebetween. A pair of robotic arms 90 are slidingly disposed about each of the tracks 88 and extend upwardly from the corresponding support rails 82 to a testing end 92.

Each of the robotic arms 90 include a third motor assembly 94 in communication with the computer 46 and coupled with the track 88 for establishing sliding movement of the arms 90 along the track 88 wherein the arms 90 are disposed at the corresponding first and second ends 84, 86 of the support rail 82 in the resting position. Each of the robotic arms 90 include a sensor assembly 96 pivotably disposed about the testing end 92 and in electrical communication with the computer 46. The sensor assemblies 96 are triangular and define an angled sensor surface 98. The sensor assemblies 96 of each of the pair of arms 90 include a thermography sensor 100 and an ultrasound sensor 102 and a plurality of optical spectroscopy sensors 104, 106 disposed along at least one of the sensor surfaces 98 and in communication with the computer 46 for correspondingly performing the thermography test 60 and the ultrasound test 64 and the optical spectroscopy test 62. The plurality of optical spectroscopy sensors 104, 106 include at least one transmitter 104 having an infrared light source and a plurality of receivers 106.

The diagnostic assembly 58 includes a contour recorder 108 in communication with the computer 46 for taking and storing a contour-shape of the breast in response to the start signal. The contour recorder 108 could be a camera, scanner, ultrasound sensor connected to a robot, or any other comparable device. The plurality of programs include a first contour analysis program 110 for analyzing the contour-shape to generate and store a 3D model 112 of the breast having at least one testing coordinate 114 relative to a mass of the breast. The plurality of programs include a second contour analysis 116 program for analyzing the contour-shape to locate an areola of the breast for establishing a primary reference point 118 of the 3D model 112 wherein the testing coordinate 114 is relative to the primary reference point 118. In other words, the contour recorder 108 will ultimately provide an accurate 3D model 112 of the breast that will allow the diagnostic assembly 58 to normalize data for the breast, and provide for a relative testing coordinate 114 that will be the relative for each of the different modalities on the same breast or be relative for a left or a right breast having different sizes.

The plurality of computer programs 54, 56, 110, 116, 120, 122, 124, 126, 128 include a robotic computer program 120 for retrieving the at least one testing coordinate 114 and operating the motor assemblies 72, 80, 94 to sequentially dispose the robotic arm 90 and the sensor assembly 96 at the testing coordinate 114. The robotic computer program 120 places the robotic arm 90 at the at least one testing coordinate 114 with pinpoint accuracy. In the preferred embodiment, the at least one testing coordinate 114 includes at least one thermography testing coordinate 114 and at least one optical spectroscopy testing coordinate 114 and at least one ultrasound testing coordinate 114.

The plurality of computer programs 54, 56, 110, 116, 120, 122, 124, 126, 128 include a thermography diagnostic program 122 for initiating the thermography sensor 100 when the robotic arm 90 and the thermography sensor 100 are disposed at the testing coordinate 114 to receive thermography data of the breast at the testing coordinate 114. The thermography diagnostic program 122 also converts the thermography data into digital temperature data points and stores the digital temperature data points along with the associated testing coordinate 114 in the memory 50. In an alternative embodiment, the thermography diagnostic program 122 could convert the thermography data into 16 colors and 256 gray scales replicating a conventional thermogram. Subsequently, the thermography diagnostic program could compare patterns in the 16 colors and 256 gray scales to common vascular patterns using an image analysis program to further identify potential breast cancer. In addition, the conversion of thermography data into digital temperature data points facilitates the analysis of the discrete temperature values in software as compared to a thermogram which would lump the thermography data into a color based on increments of 1.1 degree F.

The plurality of computer programs 54, 56, 110, 116, 120, 122, 124, 126, 128 include an optical spectroscopy diagnostic program 124 for initiating the optical spectroscopy sensors 100, 102 when the robotic arm 90 and the optical spectroscopy sensors 100, 102 are disposed at the testing coordinate 114 to receive optical spectroscopy data of the breast at the testing coordinate 114. In operation, the optical spectroscopy sensors 100, 102 pass an infrared light beam from the infrared light source into the breast and receive the optical spectroscopy data including transmitted and reflected light data at the plurality of receivers 106. The robotic arm 90 facilitates the introduction of the infrared light beam into the breast along multiple planes. In addition, the optical spectroscopy diagnostic program 124 then converts the transmitted and reflected light data into digital oxygenated hemoglobin data points and stores the digital oxygenated hemoglobin data points along with the associated testing coordinate 114 in the memory 50. Typically, when breast cancer occurs, the ratio of oxygenated or deoxygenated hemoglobin for a woman without breast cancer as compared to a woman with breast cancer increases up to 2.2:1 as a result of greater vascularization and oxygen consumption. This effect plus changes in cytochrome-c-oxidase, melanin, bilirubin, water, glucose can be quantified by measuring reflected/transmitted infrared light at frequencies of 690, 750, 788, 856 and 1310 nanometers through the breast. In other words, at a given frequency the presence of a tumor in the breast absorbs the transmitted light passed into the breast from the infrared light beam. The diagnostic assembly 58 is advantageous because it is able to associate the digital oxygenated hemoglobin data points with a pinpoint location of the breast, i.e. the testing coordinate 114.

The plurality of computer programs 54, 56, 110, 116, 120, 122, 124, 126, 128 include an ultrasound diagnostic computer program 126 for initiating the ultrasound sensor 102 when the robotic arm 90 and the ultrasound sensor 102 are disposed at the testing coordinate 114 to receive breast density data of the breast at the testing coordinate 114. The ultrasound diagnostic program converts the breast density data into digital breast density data points having a value between 1 and 100 with the digital breast density data points being proportional and corresponding to the density of the breast. The ultrasound diagnostic computer program 126 stores the digital breast density data points along with the associate testing coordinate 114 in the memory 50. The ultrasound sensor 102 is able to send an ultrasonic signal into the breast which will penetrate up to 20 cm into the breast. Based on a measurement of the reflected amount of ultrasonic signal that is returned to the ultrasonic sensor and a recording of a time of flight of the ultrasonic signal, a breast density is calculated at the testing coordinate 114. The ultrasonic diagnostic computer program 126 is advantageous because it is able to measure breast density on all sides of the breast and thus covers 99% of all potential tumor locations. In addition, clinical ultrasound uses expensive equipment and sophisticated software with 2D and 3D images. In contradistinction, the ultrasound diagnostic computer program 126 converts and records a digital number corresponding to breast density at each location and depth.

The plurality of computer programs 54, 56, 110, 116, 120, 122, 124, 126, 128 also include a data analysis program 128 for analyzing the interrelationship of the digital temperature data points and the digital oxygenated hemoglobin data points and the digital breast density data points at each of the testing coordinates 114 to detect the spatial position of a potential breast cancer within the breast. The cross-analysis of data at the testing coordinate 114 from a plurality of modalities each having a different modality improves accuracy of the test results. In addition, the data analysis program 128 will compare digital numbers or data points making the software simple and reliable, thus eliminating human interpretation of colors or patterns.

The invention also includes a method of performing a diagnostic test of the type for detecting the position of potential breast cancer in a breast of a patient using a contour recorder 108 and a test unit 22 having a computer 46 and a memory 50 and a plurality of computer programs and a diagnostic assembly 58 including at least one robotic arm 90 having a thermography sensor 100 and an ultrasound sensor 102 and a plurality of optical spectroscopy sensors 104, 106 including an infrared light source and a plurality of receivers 106.

The method comprises the steps of requesting the patient to complete a questionnaire for ascertaining family and personal medical histories and storing the family and personal medical histories in the computer 46. The patient is then disposed in a prone position on the test unit 22 for allowing the breast of the patient to hang pendant through a window opening 42 of the test unit 22. A presentation is displayed on a graphical user interface 52 for establishing communication with the patient, and a start signal is generated in response to the patient being disposed in the prone position and interacting with the graphical user interface 52.

The method proceeds by taking and storing a contour-shape of the breast in response to the start signal, and analyzing the contour-shape to generate and store a 3D model 112 of the breast having at least one testing coordinate 114 relative to a mass of the breast. The contour shape analysis also includes analyzing the contour-shape to locate an areola of the breast to establish a primary reference point 118 of the 3D model 112 wherein the testing coordinate 114 is relative to the primary reference point 118.

The method proceeds by positioning the robotic arm 90 sequentially at the testing coordinate 114, and initiating at least one diagnostic test 60, 62, 64 at the at least one testing coordinate 114. The thermography sensor 100 is initiated when the robotic arm 90 is disposed at a testing coordinate 114, and the thermography sensor 100 receives temperature data of the breast at the associated testing coordinate 114. The temperature data is then converted into digital temperature data points which are stored along with the associated testing coordinate 114 in the memory 50 of the computer 46. Before proceeding, the digital temperature data point is compared to a predetermined thermal amplification value to generate a thermal amplification signal when the digital temperature data is greater than the predetermined thermal amplification value. If this is the case, the thermography test 60 is repeated at the testing coordinate 114 in response to the thermal amplification signal. The amplification signal provides for acquiring approximately ten times more temperature data points at the suspicious location.

The method proceeds by initiating the optical spectroscopy sensors 100, 102 and the infrared light source when the robotic arm 90 is disposed at the testing coordinate 114. Accordingly, an infrared light beam is passed into the breast at the testing coordinate 114, and transmitted and reflected light data is received at each of the receivers 106.

The transmitted and reflected light data is converted into digital oxygenated or deoxygenated hemoglobin data points which are stored along with the associated testing coordinate 114 in the memory 50 of the computer 46. Before proceeding, the digital hemoglobin data is compared to a predetermined optical spectroscopy amplification value to generate an optical spectroscopy amplification signal when the digital oxygenated hemoglobin data is greater than the predetermined optical spectroscopy amplification value. For example, the predetermined optical spectroscopy amplification value could be the oxygenated or deoxygenated hemoglobin data, or even other breast characteristics such as lipids or water, at the relative testing coordinate of the opposing breast. If this is the case, the optical spectroscopy test 62 is repeated at the optical spectroscopy coordinate in response to the spectroscopy amplification signal, and approximately ten times more data is acquired at the suspicious location.

The method proceeds by initiating the ultrasound sensor 102 when the robotic arm 90 is disposed at the testing coordinate 114 to send an ultrasonic signal into the breast. A reflected amount of the ultrasonic signal is then returned to the ultrasonic sensor, and the time of flight of the ultrasonic signal is recorded. Subsequently, a breast density is calculated at the associate testing coordinate 114 as a function of the reflected amount of ultrasonic signal and the time of flight. The breast density is converted into a digital breast density data point having a value between 1 and 100 with the digital breast density data point being proportional and corresponding to the breast density of the breast. The digital breast density data point is then stored along with the associated testing coordinate 114 in the memory 50 of the computer 46. Before proceeding the digital breast density data point is compared to a predetermined ultrasound amplification value to generate an ultrasound amplification signal when the digital ultrasound number is greater than the predetermined ultrasound amplification value. If this is the case, the ultrasound test 64 is repeated at the ultrasound coordinate in response to the ultrasound amplification signal. For example, when a suspicious area is examined, the sensor angle can be changed to estimate density at the same location from different angles to triangulate the position and improve results. In addition, an elastography test could be performed at the testing coordinate 114 wherein the robotic arm 90 presses against the breast in the suspicious area and the ultrasound sensor 64 determines whether a potential tumor stays solid indicating that the tumor is malignant or whether the potential tumor opens up into a doughnut shape indicating that the tumor is benign.

When the diagnostic tests 60, 62, 64 are complete, the patient is removed from the test unit 22 and the examination table. Subsequently, a data analysis program 128 analyzes the interrelationship of the digital temperature data points and the digital oxygenated hemoglobin data points and the digital breast density data points at the testing coordinate 114 to detect the spatial position of a potential breast cancer within the breast. The cross-analysis of data from a plurality of diagnostic tests 60, 62, 62 each having a different modality improves accuracy of the test results. In addition, the data analysis program 128 will compare digital numbers or data points making the software simple and reliable, thus eliminating human interpretation of colors or patterns.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A multi-modality breast cancer test assembly (20) of the type for detecting the position of potential cancer in a breast of a patient being supported in a prone position along an examination table in an examination room, said assembly comprising;
   a test unit (22) having an interior (36) for receiving the breast of the patient,
   a computer (46) connected to said test unit (22) and including a processor (48) and a memory (50) and a plurality of computer programs (54, 56, 110, 116, 120, 122, 124, 126, 128),
   a contour recorder (108) for taking and storing a contour-shape of the breast,
   said plurality of programs (54, 56, 110, 116, 120, 122, 124, 126, 128) including a first contour analysis program (110) for analyzing said contour-shape to generate and store a 3D model (112) of the breast having at least one testing coordinate (114) relative to a mass of the breast,
   a diagnostic assembly (58) disposed within said interior (36) of said test unit (22) and in electrical communication with said computer (46) and including a plurality of sensors for performing a plurality of diagnostic tests (60, 62, 64) each having a different modality on the breast,
   said plurality of computer programs (54, 56, 110, 116, 120, 122, 124, 126, 128) including at least one diagnostic program (122, 124, 126) for initiating at least one of said diagnostic tests (60, 62, 64) at said testing coordinate (114),
   said plurality of computer programs (54, 56, 110, 116, 120, 122, 124, 126, 128) including a data analysis program (128) for analyzing the interrelationship of said plurality of diagnostic tests (60, 62, 64) at said testing coordinate (114) to detect the spatial position of a potential breast cancer within the breast;
   said plurality of sensors (100, 102, 104, 106) including at least one thermography sensor (100) and at least one optical spectroscopy sensor (104, 106) and at least one ultrasound sensor (102) for correspondingly performing a thermography test (60) and an optical spectroscopy test (62) and an ultrasound test (64) on the breast;
   said at least one diagnostic program (122, 124, 126) including a thermography diagnostic program (122) for receiving thermography data and converting said thermography data into digital temperature data points of the breast and storing said digital temperature data points along with said associated testing coordinate (114) in said memory (50),
   said at least one diagnostic program (122, 124, 126) including an optical spectroscopy diagnostic program (124) for receiving optical spectroscopy data and converting said optical spectroscopy data into digital oxygenated or deoxygenated hemoglobin data points of the breast and storing said digital oxygenated or deoxygenated hemoglobin data points along with said associated testing coordinate (114) in said memory (50),
   said at least one diagnostic program (122, 124, 126) including an ultrasound diagnostic program for receiving ultrasound data and converting said ultrasound data into digital breast density data points having a breast density value between 1 and 100 which corresponds to the density of the breast and storing said digital breast density data points along with said associated testing coordinate (114) in said memory (50).

2. An assembly as set forth in claim 1 wherein said plurality of computer programs (54, 56, 110, 116, 120, 122, 124, 126, 128) include a second contour analysis (116) program for analyzing said contour-shape to locate an areola of the breast for establishing a primary reference point (118) of said 3D model (112) wherein said testing coordinate (114) is relative to said primary reference point (118).

3. An assembly as set forth in claim 2 further comprising; said diagnostic assembly (58) including at least one robotic arm (90) for receiving said plurality of sensors (100, 102, 104, 106),
said robotic arm (90) including a robot motor assembly (72, 80, 94) in communication with said computer (46) for establishing movement of said robotic arm (90) within said interior (36) of said test unit (22),
said plurality of programs including a robotic computer program (120) for retrieving said at least one testing coordinate (114) and operating said motor assembly (72, 80, 94) to sequentially dispose said robotic arm (90) at said testing coordinate (114).

4. An assembly as set forth in claim 3 further comprising; said test unit (22) extending between a bottom surface (24) and a top surface (26) to define front and rear and left and right sides (32, 34) and said interior (36) disposed inwardly from said surfaces (24, 26) and said sides (28, 30, 32, 34),
a plurality of caster wheels (38) attached to said bottom surface (24) for establishing rolling movement over ground in the examination room to dispose said rear side (30) of said test unit (22) in abutting relationship with the examination table for receiving the patient in the prone position along said top surface (26),
said top surface (26) defining a window opening (42) for pendantly receiving the breast of the patient within said interior (36) of said test unit (22).

5. An assembly as set forth in claim 4 further comprising; a face support (44) hingedly attached to said front side (28) and disposed next adjacent said top surface (26) for supporting a head of the patient in the prone position,
a graphical user interface (52) extending outwardly from said front side (28) of said test unit (22) and disposed below said face support (44) and in electrical communication with said computer (46) for establishing communication with the patient disposed in the prone position.

6. An assembly as set forth in claim 5 further comprising; said plurality of computer programs (54, 56, 110, 116, 120, 122, 124, 126, 128) including a patient information program (54) for displaying a questionnaire on said graphical user interface (52) and receiving a plurality of patient inputs in response to said questionnaire for storage within said memory (50) of said computer (46),
said plurality of computer programs (54, 56, 110, 116, 120, 122, 124, 126, 128) including a patient analysis program (56) for evaluating said patient inputs and generating a start signal in response to completing the evaluation.

7. A multi-modality breast cancer test assembly (20) of the type for detecting the position of potential cancer in a breast of a patient being supported in a prone position along an examination table in an examination room, said assembly comprising;
a test unit (22) having an interior (36) for receiving the breast of the patient,
said test unit (22) extending between a bottom surface (24) and a top surface (26) to define front and rear and left and right sides (32, 34) and said interior (36) disposed inwardly from said surfaces (24, 26) and said sides (28, 30, 32, 34),
a computer (46) connected to said test unit (22) and including a processor (48) and a memory (50) and a plurality of computer programs (54, 56, 110, 116, 120, 122, 124, 126, 128),
a contour recorder (108) for taking and storing a contour-shape of the breast,
said plurality of programs (54, 56, 110, 116, 120, 122, 124, 126, 128) including a first contour analysis program (110) for analyzing said contour-shape to generate and store a 3D model (112) of the breast having at least one testing coordinate (114) relative to a mass of the breast,
a diagnostic assembly (58) disposed within said interior (36) of said test unit (22) and in electrical communication with said computer (46) and including a plurality of sensors for performing a plurality of diagnostic tests (60, 62, 64) each having a different modality on the breast,
said plurality of computer programs (54, 56, 110, 116, 120, 122, 124, 126, 128) including at least one diagnostic program (122, 124, 126) for initiating at least one of said diagnostic tests (60, 62, 64) at said testing coordinate (114),
said plurality of computer programs (54, 56, 110, 116, 120, 122, 124, 126, 128) including a data analysis program (128) for analyzing the interrelationship of said plurality of diagnostic tests (60, 62, 64) at said testing coordinate (114) to detect the spatial position of a potential breast cancer within the breast;
said plurality of sensors (100, 102, 104, 106) including at least one thermography sensor (100) and at least one optical spectroscopy sensor (104, 106) and at least one ultrasound sensor (102) for correspondingly performing a thermography test (60) and an optical spectroscopy test (62) and an ultrasound test (64) on the breast;
said plurality of computer programs (54, 56, 110, 116, 120, 122, 124, 126, 128) include a second contour analysis (116) program for analyzing said contour-shape to locate an areola of the breast for establishing a primary reference point (118) of said 3D model (112) wherein said testing coordinate (114) is relative to said primary reference point (118);
said diagnostic assembly (58) including at least one robotic arm (90) for receiving said plurality of sensors (100, 102, 104, 106),
said robotic arm (90) including a robot motor assembly (72, 80, 94) in communication with said computer (46) for establishing movement of said robotic arm (90) within said interior (36) of said test unit (22),
said plurality of programs including a robotic computer program (120) for retrieving said at least one testing coordinate (114) and operating said motor assembly (72, 80, 94) to sequentially dispose said robotic arm (90) at said testing coordinate (114);
said diagnostic assembly (58) including at least one mechanical support (66) disposed about one of said surfaces (24, 26) or said sides (28, 30, 32, 34) for supporting said diagnostic assembly (58) within said interior (36) of said test unit (22),
said diagnostic assembly (58) including a base member (68) disposed about said mechanical support (66),
said diagnostic assembly (58) including at least one support post (76) extending upwardly from said base member (68) to a rail end (78), said support post (76) including a support rail (82) extending about said rail end (78) between a first end (84) and a second end (86) and having tracks (88) extending therebetween, said robotic arm (90) slidingly disposed about said tracks (88), said robot motor assembly (72, 80, 94) including a first motor assembly (72) mechanically coupled between said mechanical support (66) and said base member (68) and a second motor assembly (80) coupled with said support post (76) and a third motor assembly (94) coupled between said robotic arm (90) and said track (88) for collectively establishing said movement of said robotic arm (90) about said interior (36) of said test unit (22) wherein said first motor assembly (72) establishes movement of said base member (68) along said mechanical support (66) and said second motor assembly (80) establishes at least 270 degree rotational movement of said support post (76) and said third motor assembly (94) establishes sliding movement of said arm along said track (88).

8. An assembly as set forth in claim 7 wherein said robotic arm (90) extends upwardly from said support rail (82) to a testing end (92) and includes a sensor assembly (96) pivotably disposed about said testing end (92) to define a sensor surface (98) for receiving said thermography and ultrasound and optical spectroscopy sensors (100, 102, 104, 106) along said surface.

9. A multi-modality breast cancer test assembly (20) of the type for detecting the position of potential cancer in a left or a right breast of a patient being supported in a prone position along an examination table in an examination room, said assembly comprising;

a test unit (22) being rectangular and extending between a bottom surface (24) and a top surface (26) to define front and rear sides (28, 30) having a test unit length ($L_t$) being less than or equal to 36 inches and left and right sides (32, 34) having a test unit width ($W_t$) being less than or equal to 25 inches and an interior (36) being hollow and disposed inwardly from said surfaces (24, 26) and said sides (28, 30, 32, 34), a plurality of caster wheels (38) attached to said bottom surface (24) for establishing rolling movement over ground in the examination room to dispose said rear side (30) of said testing unit in abutting relationship with the examination table for receiving the patient in the prone position along said top surface (26) of said test unit (22), each of said caster wheels (38) including a locking mechanism (40) for preventing movement of said abutting test unit (22), said top surface (26) defining a window opening (42) for pendantly receiving the breast of the patient within said interior (36) of said test unit (22), a face support (44) hingedly attached to said front side (28) of said test unit (22) and disposed next adjacent said top surface (26) for supporting a head of the patient in the prone position, a computer (46) connected to said test unit (22) and including a processor (48) and a memory (50) and a plurality of computer programs (54, 56, 110, 116, 120, 122, 124, 126, 128), a graphical user interface (52) extending outwardly from said front side (28) of said test unit (22) and disposed below said face support (44) and in electrical communication with said computer (46) for establishing communication with the patient disposed in the prone position, said plurality of computer programs (54, 56, 110, 116, 120, 122, 124, 126, 128) including a patient information program (54) for displaying a questionnaire on said computer (46) and receiving a plurality of patient inputs in response to said questionnaire for storage within said memory (50) of said computer (46), said plurality of computer programs (54, 56, 110, 116, 120, 122, 124, 126, 128) including a patient analysis program (56) for evaluating said patient inputs and generating a start signal in response to completing the evaluation, a diagnostic assembly (58) disposed within said interior (36) of said testing unit and in electrical communication with said computer (46) for performing a plurality of diagnostic tests (60, 62, 64) on the pendant breast in response to said start signal, said plurality of diagnostic tests (60, 62, 64) including a thermography test (60) and an optical spectroscopy test (62) and an ultrasound test (64), said diagnostic assembly (58) including at least one mechanical support (66) extending along said rear side (30) of said test unit (22) between said top surface (26) and said bottom surface (24) for supporting said diagnostic assembly (58) within said interior (36) of said test unit (22), said diagnostic assembly (58) including a base member (68) disposed about said mechanical support (66), said base member (68) including a cross member (70) disposed in sliding engagement with said mechanical support (66) and extending perpendicularly to said mechanical support (66), said base member (68) including a first motor assembly (72) in communication with said computer (46) and mechanically coupled with said mechanical support (66) for moving said base member (68) along said mechanical support (66) from an initial resting position wherein said diagnostic assembly (58) is disposed next adjacent said bottom surface (24), said base member (68) including a base plate (74) disposed about said cross member (70), a plurality of support posts (76) extending upwardly from said base plate (74) to a rail end (78) and each of said support posts (76) including a second motor assembly (80) in communication with said computer (46) for establishing at least 270 degree rotational movement of said support posts (76), each of said support posts (76) including a support rail (82) extending perpendicularly about said rail end (78) between a first end (84) and a second end (86) and having tracks (88) extending therebetween, a pair of robotic arms (90) slidingly disposed about each of said tracks (88) and extending upwardly from said corresponding support rails (82) to a testing end (92), each of said robotic arms (90) including a third motor assembly (94) in communication with said computer (46) and coupled with said track (88) for establishing sliding movement of said arms (90) along said track (88) wherein said arms (90) are disposed at said corresponding first and second ends (84, 86) of said support rail (82) in said resting position, each of said robotic arms (90) including a sensor assembly (96) pivotably disposed about said testing end (92) and in electrical communication with said computer (46) and said sensor assembly (96) being triangular to define a sensor surface (98) being angled, said sensor assemblies (96) of each of said pair of arms (90) including at least one of a thermography sensor (100) and an ultrasound sensor (102) and an optical spectroscopy sensor (104, 106) disposed along said sensor surface (98) and in communication with said computer (46) for correspondingly performing said thermography test (60) and said ultrasound test (64) and said optical spectroscopy test (62), said plurality of optical spectroscopy sensors (104, 106) including a transmitter (104) having an infrared light source and a plurality of receivers (106), a contour recorder (108) in communication with said computer (46) for taking and storing a contour-shape of the breast in response to said start signal, said plurality of computer programs (54, 56, 110, 116, 120, 122, 124, 126, 128) including a first contour analysis program (110) for analyzing said contour-shape to generate and store a 3D model (112) of the breast having at least one testing coordinate (114) relative to a mass of the breast, said plurality of computer programs (54, 56, 110, 116, 120, 122, 124, 126, 128) including a second contour analysis (116) program for analyzing said contour-shape to locate an areola of the breast for establishing a primary reference point (118) of said 3D model (112) wherein said testing coordinate (114) is relative to said primary reference point (118), said plurality of computer programs (54, 56, 110, 116, 120, 122, 124, 126, 128) including a robotic computer program (120) for retrieving said at least one testing coordinate (114) and operating said motor assemblies (72, 80, 94) to sequentially dispose said robotic arm (90) and said sensors (100, 102) at said testing coordinate (114), said plurality of computer programs (54, 56, 110, 116, 120, 122, 124, 126, 128) including a thermography diagnostic program (122) for initiating said thermography sensor (100) when said robotic arm (90) and said sensor are disposed at said testing coordinate (114) to receive thermography data of the corresponding breast at said testing coordinate (114) and for converting said thermography data into digital temperature data points and for storing said digital temperature data points along with said associated testing coordinate (114) in said memory (50), said plurality of computer programs (54, 56, 110, 116, 120, 122, 124, 126, 128) including an optical spectroscopy program for initiating said optical spectroscopy sensors (100, 102) when said robotic arm (90) and said sensors (100, 102) are disposed at said testing coordinate (114) to pass an infrared light beam from said infrared light source into the breast and to receive optical spectroscopy data including transmitted and reflected light data at said plurality of receivers (106) at said testing coordinate (114) and for converting said transmitted and reflected light data into digital oxygenated or deoxygenated hemoglobin data points and storing said digital oxygenated or dexoxygenated hemoglobin data points along with said associated testing coordinate (114) in said memory (50), said plurality of computer programs (54, 56, 110, 116, 120, 122, 124, 126, 128) including an ultrasound diagnostic computer program (126) for initiating said ultrasound sensor (102) when said robotic arm (90) and said ultrasound sensor (102) are disposed at said testing coordinate (114) to receive breast density data of the breast at said testing coordinate (114) and for converting said breast density data into digital breast density data points having a value between 1 and 100 with said digital breast density data points being proportional and corresponding to the density of the breast and storing said digital breast density data points along with said associate testing coordinate (114) in said memory (50), and characterized by said plurality of computer programs (54, 56, 110, 116, 120, 122, 124, 126, 128) including a data analysis program (128) for analyzing the interrelationship of said digital temperature data points and said digital oxygenated or deoxygenated hemoglobin data points and said digital breast density data points at each of said testing coordinates (114) to detect the spatial position of a potential breast cancer within the breast.

\* \* \* \* \*